United States Patent [19]

Miyamoto et al.

[11] Patent Number: 5,877,168
[45] Date of Patent: Mar. 2, 1999

[54] VITAMIN D DERIVATIVE WITH SUBSTITUENT AT THE 2β-POSITION

[75] Inventors: Katsuhito Miyamoto, Tokyo; Noboru Kubodera, Shizuoka-ken, both of Japan

[73] Assignee: Chugai Seiyaku Kabushiki Kaisha, Tokyo, Japan

[21] Appl. No.: 706,969

[22] Filed: Sep. 3, 1996

Related U.S. Application Data

[63] Continuation of Ser. No. 386,544, Feb. 10, 1995, abandoned.
[51] Int. Cl.$^6$ .......................... A61K 31/59; C07C 401/00
[52] U.S. Cl. ........................................ 514/167; 552/653
[58] Field of Search ............................. 552/653; 514/167

[56] References Cited

U.S. PATENT DOCUMENTS

| | | | |
|---|---|---|---|
| 4,011,250 | 3/1977 | Ishiwaka et al. | |
| 5,389,622 | 2/1995 | Posner et al. | 514/167 |
| 5,661,140 | 8/1997 | DeLuca et al. | 514/167 |

FOREIGN PATENT DOCUMENTS

| | | |
|---|---|---|
| 0619306 | 10/1994 | European Pat. Off. |
| 100043 | 8/1975 | Japan |
| 100044 | 8/1975 | Japan |
| 641059 | 2/1994 | Japan |
| 8103023 | 10/1981 | WIPO |
| 8202893 | 9/1982 | WIPO |

OTHER PUBLICATIONS

Gary H. Posner et al, Stereocontrolled Total Synthesis of Calcitriol . . . Drug J.Org. Chem. vol. 59, pp. 7855–7861, 1994.

Primary Examiner—José G. Dees
Assistant Examiner—Barbara Badio
Attorney, Agent, or Firm—Browdy And Neimark

[57] ABSTRACT

A 1α-hydroxy-vitamin D derivative represented by formula (I):

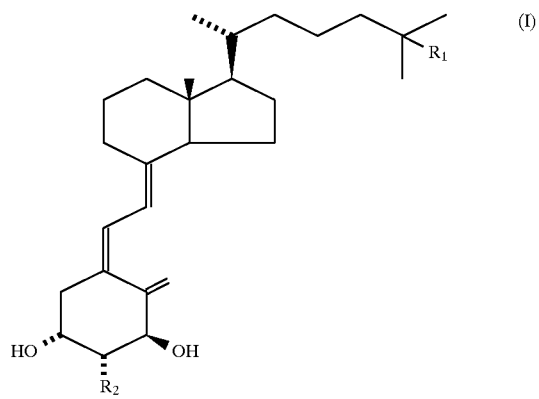

wherein $R_1$ represents a hydrogen atom or a hydroxyl group; and $R_2$ represents a straight-chain or branched lower alkyl, lower alkenyl or lower alkynyl group, which is substituted with a hydroxyl group, a halogen atom, a cyano group, a lower alkoxy group, an amino group or an acylamino group, is disclosed. The compound exhibits calcium metabolism regulating activity and differentiation stimulating activity on tumor cells, etc. and is useful as a treating agent for diseases caused by abnormal calcium metabolism, such as osteoporosis and osteomalacia, or as an antitumor agent.

13 Claims, 4 Drawing Sheets

VITAMIN D DERIVATIVE WITH SUBSTITUENT AT THE 2β-POSITION

CROSS REFERENCE TO RELATED APPLICATIONS

This application is a continuation of application Ser. No. 08/386,544, filed Feb. 10, 1995, now abandoned.

FIELD OF THE INVENTION

This invention relates to a novel vitamin D derivative which has an in vivo calcium regulatory activity and a differentiation stimulating activity on tumor cells, etc. and is useful as a treating agent for diseases caused by abnormal calcium metabolism, such as osteoporosis and osteomalacia, or as an antitumor agent. More particularly, it relates to a vitamin $D_3$ derivative having a substituted or unsubstituted lower alkyl, lower alkenyl or lower alkynyl group at the 2β-position.

BACKGROUND OF THE INVENTION

Conventionally known vitamin $D_3$ derivatives include natural metabolites, such as 25-hydroxyvitamin $D_3$ and 1α,25-dihydroxyvitamin $D_3$, and synthetic analogues thereof, such as 1α-hydroxyvitamin $D_3$, 1α,24-dihydroxyvitamin $D_3$, and various fluorinated vitamin $D_3$ derivatives. Of these vitamin $D_3$ derivatives, 1α,25-dihydroxyvitamin $D_3$, 26,27-hexafluoro-1α,25-dihydroxyvitamin $D_3$, etc. are known to have a potent calcium metabolism regulating activity and be useful for various osseous lesions.

Known vitamin $D_3$ derivatives having a substituent at the 2β-position include 1α,25-dihydroxy-2β-fluorovitamin $D_3$ disclosed in Japanese Patent Publication (Kokoku) No. 14303/91 and the derivatives having a substituted lower alkoxy group at the 2β-position disclosed in Japanese Patent Application Laid Open (Kokai) No. 267549/86.

The in vivo metabolic pathways of natural type vitamin $D_3$ derivatives such as the known active metabolites have been established so that there are limits of dose in administration of these vitamin $D_3$ derivatives as drugs. The non-natural type fluorinated vitamin $D_3$ derivatives involve complicatedness of fluorine introduction in the preparation thereof. Besides, the fluorinated derivatives are expected to be less susceptible to metabolism in a living body and be apt to retained in the body, causing side effects.

Vitamin $D_3$ derivatives with a substituted lower alkoxy group at the 2β-position have a possibility that the substituent may be cut off by in vivo metabolism because it is introduced through an ether linkage.

SUMMARY OF THE INVENTION

As a result of extensive investigations, the present inventors have found that a substituted or unsubstituted lower alkyl group, lower alkenyl group or lower alkynyl group can easily be introduced to the 2β-position of vitamin D through a carbon-carbon bond by a reaction using an organometallic compound, such as a Grignard reagent or organic lithium. The present invention has been reached based on this finding.

DETAILED DESCRIPTION OF THE INVENTION

Figure 1:
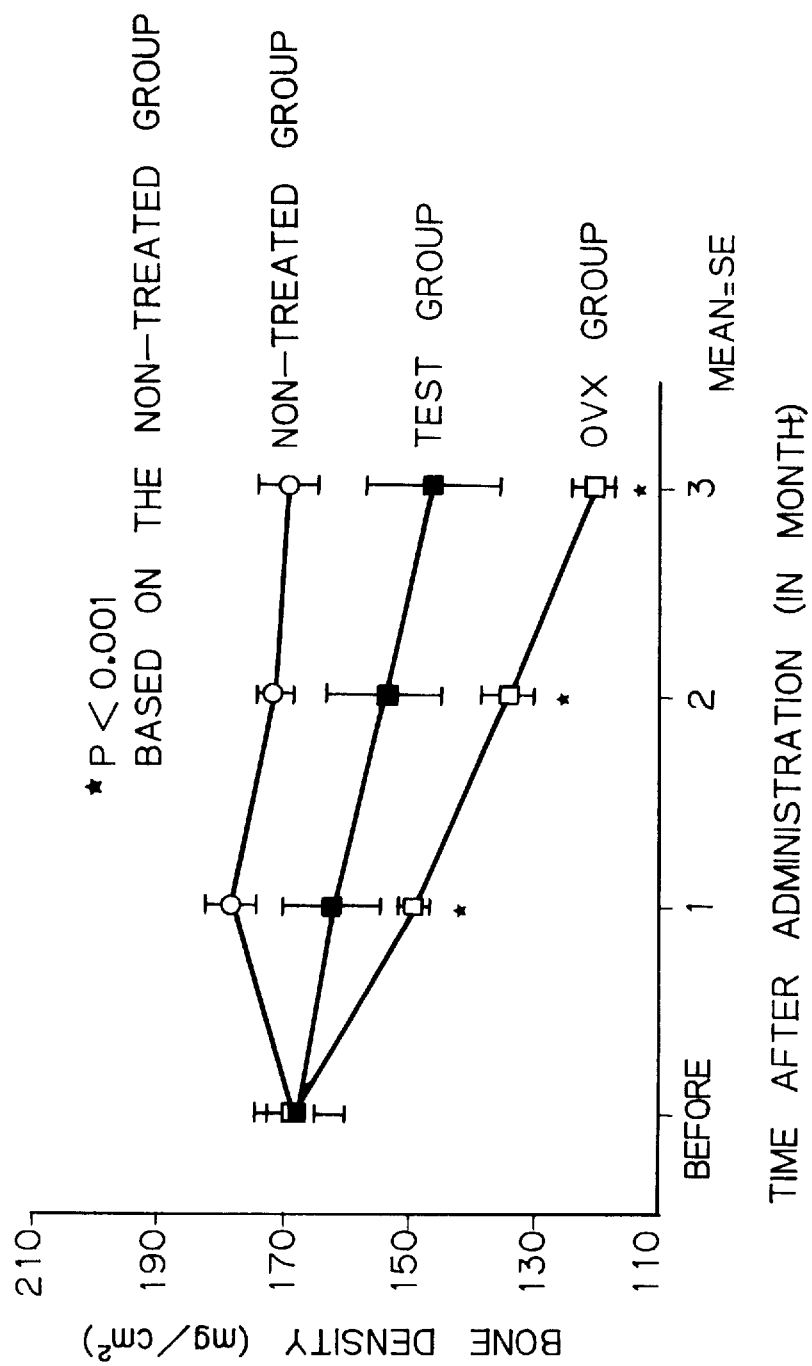
FIG. 1 is a graph showing changes of bone density with time in a test group which underwent ovariectomy (OVX) and received the drug of Example 2, a non-treated group, and an OVX group which underwent OVX and received no drug.

The present invention provides a vitamin $D_3$ derivative represented by formula (I):

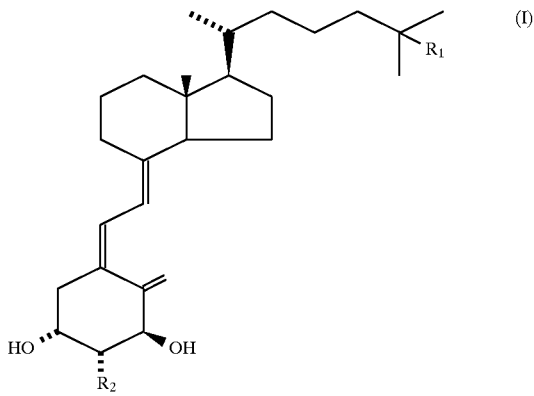

wherein $R_1$ represents a hydrogen atom or a hydroxyl group; and $R_2$ represents a straight-chain or branched lower alkyl, lower alkenyl or lower alkynyl group, each of which may be substituted with a hydroxyl group, a halogen atom, a cyano group, a lower alkoxy group, an amino group or an acylamino group.

The term "lower alkyl group" as used herein means a straight-chain or branched carbon chain having 1 to 7 carbon atoms, e.g., methyl, ethyl, propyl, n-butyl, isobutyl, n-pentyl or n-hexyl. The term "lower alkenyl group" as used herein means a straight-chain or branched carbon chain having 2 to 7 carbon atoms and at least one double bond, e.g., vinyl, allyl, butenyl or pentenyl. The term "lower alkynyl group" as used herein means a straight-chain or branched carbon chain having 2 to 7 carbon atoms and at least one triple bond, e.g., ethynyl, propynyl, butynyl or pentynyl. Each of the lower alkyl group, lower alkenyl group and lower alkynyl group may be substituted with a hydroxyl group, a halogen atom, a cyano group, a lower alkoxy group, an amino group or an acylamino group. The term "lower alkoxy group" as used herein means an alkyloxy group having 1 to 7 carbon atoms, preferably 1 to 3 carbon atoms, still preferably a methoxy group or an ethoxy group. The term "acylamino group" as used herein means a substituted or unsubstituted lower alkyl-carbonylamino group or a substituted or unsubstituted arylcarbonylamino group, preferably an acetylamino group. For example, $R_2$ may represent an alkyl, alkenyl or alkynyl group substituted with a hydroxyalkyl group, a haloalkyl group, an aminoalkyl group, a hydroxyalkenyl group, a haloalkenyl group, an aminoalkenyl group, a hydroxyalkynyl group, a haloalkynyl group, an aminoalkynyl group, etc.

The compound of the present invention can be prepared by, for example, reacting an epoxy compound represented by formula (II):

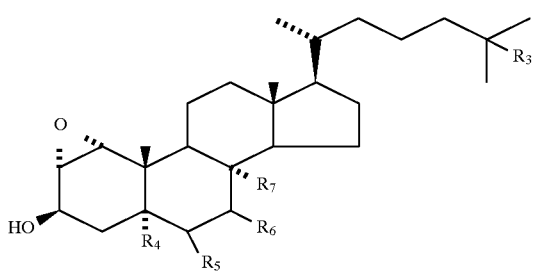

wherein $R_3$ represents a hydrogen atom, a hydroxyl group or a protected hydroxyl group; $R_4$ and $R_5$ are taken together to form a double bond, and $R_6$ and $R_7$ are taken together to form a double bond; or $R_5$ and $R_6$ are taken together to form a double bond, and $R_4$ and $R_7$ are bonded to a dienophile capable of protecting a conjugated double bond, such as 4-phenyl-1,2,4-triazoline-3,5-dione or diethyl maleate, with a compound represented by formula (III):

$$R_8MgX \quad (III)$$

wherein $R_8$ represents a straight-chain or branched lower alkyl, lower alkenyl or lower alkynyl group, each of which may be substituted with a hydroxyl group, a protected hydroxyl group, a halogen atom, a cyano group, a lower alkoxy group, an amino group or a protected amino group; and X represents a halogen atom, e.g., chlorine, bromine or iodine, or a compound represented by formula (IV):

$$R_9Li \quad (IV)$$

wherein $R_9$ represents a straight-chain or branched lower alkyl, lower alkenyl or lower alkynyl group, each of which may be substituted with a hydroxyl group, a protected hydroxyl group, a halogen atom, a cyano group, a lower alkoxy group, an amino group or a protected amino group, to obtain a provitamin $D_3$ derivative represented by formula (V):

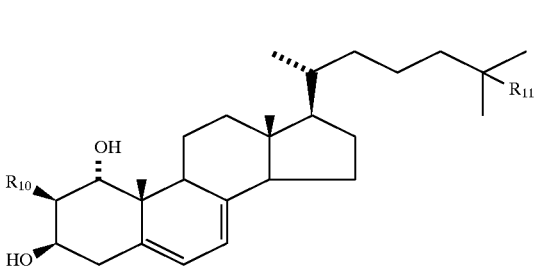

wherein $R_{10}$ represents a straight-chain or branched lower alkyl, lower alkenyl or lower alkynyl group, each of which may be substituted with a hydroxyl group, a protected hydroxyl group, a halogen atom, a cyano group, a lower alkoxy group, an amino group or a protected amino group; and $R_{11}$ represents a hydrogen atom, a hydroxyl group or a protected hydroxyl group, and subjecting the provitamin $D_3$ derivative represented by formula (V) to light irradiation and thermal isomerization according to a known process described, e.g., in Japanese Patent Application Laid Open (Kokai) No. 84555/75.

The reaction between the compound of formula (II) and the compound of formula (III) is carried out in an inert solvent, preferably an ether solvent, such as tetrahydrofuran (THF) or diethyl ether. The reaction temperature varies depending on the starting compounds, the solvent and other conditions, but is usually in the range of from $-80°$ to $80°$ C.

The compound of formula (II) can be obtained, for example, from cholesterol or 25-hydroxycholesterol in accordance with the processes disclosed in Japanese Patent Application Laid-Open (Kokai) Nos. 84555/75 and 84560/75.

The compound of formula (III) may be a commercially available Grignard reagent, or it may be prepared from a metallic magnesium and a substituted or unsubstituted alkyl, alkenyl or alkynyl halide.

The compound of formula (IV) may be a commercially available organolithium reagent, or it may be prepared from a metallic lithium and a substituted or unsubstituted alkyl, alkenyl or alkynyl halide.

A preferred embodiment of the above-mentioned process for synthesizing the compound of the present invention is shown in the reaction scheme below, in which α-epoxide (VI) is reacted with an alkenyl Grignard reagent to obtain a 2-alkenyl compound of formula (VII), the hydroxyl groups of the compound of formula (VII) are protected to obtain compound of formula (VIII), the protected compound of formula (VIII) is subjected to hydroboration to obtain a 2-alcohol compound of formula (IX), the protective groups (TES) are removed from the compound of formula (IX) to obtain a provitamin $D_3$ derivative of formula (X), and the provitamin $D_3$ derivative of formula (X) is subjected to light irradiation and thermal isomerization.

Reaction Scheme:

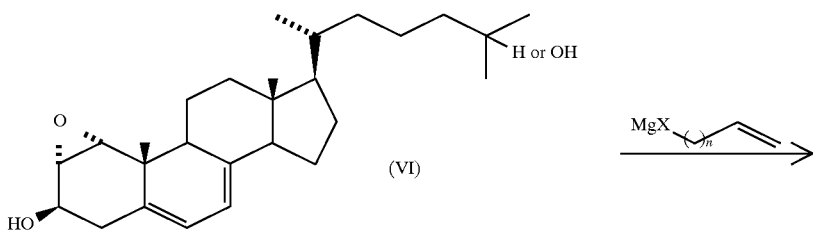

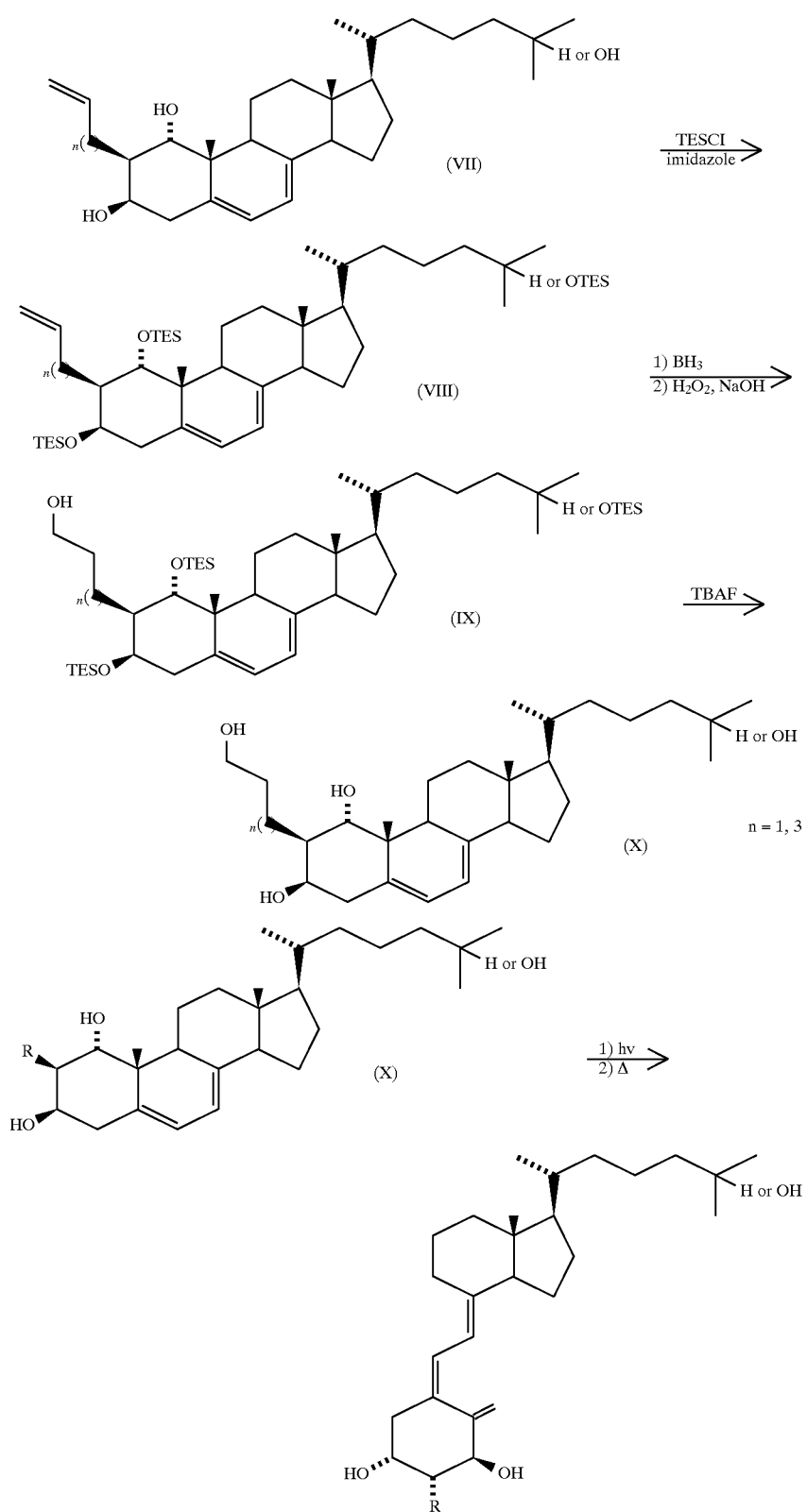
The compound according to the present invention exhibits an in vivo calcium regulating activity and a differentiation stimulating activity on tumor cells, etc. and is useful as a drug, such as a treating agent for diseases caused by abnormal calcium metabolism, e.g., osteoporosis and osteomalacia, or as an antitumor agent.

The present invention will now be illustrated in greater detail with reference to Examples and Test Examples, but it should be understood that the present invention is not construed as being limited thereto.

EXAMPLE 1

Synthesis of 2β-Ethyl-1α,3β-dihydroxy-9,10-secocholesta-5,7,10(19)-triene

1) Synthesis of 2β-Ethyl-1α,3β-dihydroxy-5,7-cholestadiene:

In 3 ml of THF was dissolved 100 mg of 1α,2α-epoxy-5α,8α-(3,5-dioxo-4-phenyl-1,2,4-triazolidino)-6-cholesten-3β-ol in an argon atmosphere, and 2 ml of a THF solution of ethylmagnesium bromide (1.01 mol/l) was added thereto. The mixture was stirred at room temperature for 19.5 hours and then heated under reflux for 4 hours. The reaction mixture was poured into water and extracted with ethyl acetate. The organic layer was washed successively with an aqueous ammonium chloride solution and an aqueous sodium chloride solution and dried over magnesium sulfate. The solvent was removed by distillation, and the residue was purified by flash column chromatography on silica gel using a 3:2 mixed solvent of n-hexane and ethyl acetate as an eluent to obtain 51.2 mg (69%) of the title compound as colorless crystals.

$^1$H-NMR (CDCl$_3$)δ: 0.62(3H,s), 0.85(3H,s), 0.88(3H,s), 0.94(3H,d,J=6.1 Hz), 1.01(3H,s), 3.80(1H,m), 4.12–4.28 (1H,m), 5.30–5.38(1H,m), 5.60–5.70(1H,m)
UV λ$_{max}$ (EtOH) nm: 293, 282, 272, 263 (sh)
MS m/z : 428 (M$^+$), 410, 342 (100%)

2) Synthesis of 2β-Ethyl-1α,3β-dihydroxy-9,10-secocholesta-5,7,10(19)-triene:

In 350 ml of ethanol was dissolved 32.6 mg of 2β-ethyl-1α,3β-dihydroxy-5,7-cholestadiene, and the solution was irradiated with light of a 400 W high-pressure mercury lamp through a Vycor filter for 180 seconds while bubbling argon gas through the solution under ice-cooling. Ethanol was removed under reduced pressure, and the residue was dissolved in 5 ml of THF. The solution was heated under reflux for 1.5 hours in a nitrogen atmosphere to remove the solvent by distillation. The resultant residue was subjected to silica gel flash column chromatography using a 7:3 mixed solvent of n-hexane and ethyl acetate as an eluent. The eluate was further purified by fractional thin layer chromatography on silica gel developing twice with a 7:3 mixture of n-hexane and ethyl acetate and twice with a 9:1 mixture of methylene chloride and ethanol to obtain 0.59 mg of the title compound.

$^1$H-NMR (CDCl$_3$)δ: 0.55(3H,s), 0.85(3H,s), 0.88(3H,s), 0.92(3H,d,J=5.9 Hz), 0.99(3H,s), 5.03(1H,s), 5.39(1H,s), 6.02(1H,d,J=11.4 Hz), 6.35(1H,d,J=11.4H)
UV λ$_{max}$ (EtOH) nm: 263
UV λ$_{min}$ (EtOH) nm: 229

EXAMPLE 2

Synthesis of 2β-(4-Hydroxybutyl)-1α,3β-dihydroxy-9,10-secocholesta-5,7,10(19)-triene 1) Synthesis of 2β-(4-Hydroxybutyl)-1α,3β-dihydroxy-5,7-cholestadiene:

To 4.3 ml of a THF solution of ethylmagnesium bromide (1.01 mol/l) cooled to −20° to −25° C. was added 400 μl of 4-chloro-1-butanol in a nitrogen atmosphere, followed by stirring at that temperature for 15 minutes. After warming the solution to room temperature, 90 mg of magnesium was added thereto, followed by heat-refluxing for 13.5 hours in a nitrogen atmosphere. After cooling the reaction mixture to room temperature, a solution of 100 mg of 1α,2α-epoxy-5α,8α-(3,5-dioxo-4-phenyl-1,2,4-triazolidino)-6-cholesten-3β-ol in 3 ml of TFH was added thereto, followed by heat-refluxing for 1 hour in a nitrogen atmosphere. The reaction mixture was poured into an aqueous ammonium chloride solution and extracted with ethyl acetate. The organic layer was washed with an aqueous sodium chloride solution, dried over magnesium sulfate, and evaporated to remove the solvent. The resultant residue was subjected to silica gel flash column chromatography using ethyl acetate to obtain 36.8 mg (45%) of the title compound as colorless crystals.

$^1$H-NMR (CDCl$_3$)δ: 0.63(3H,s), 0.85(3H,s), 0.89(3H,s), 0.95(3H,d,J=6.1 Hz), 1.00(3H,s), 5.30–5.40(1H,m), 5.58–5.68(1H,m)
UV λ$_{max}$ (EtOH) nm: 293, 282, 272, 263 (sh)
MS m/z : 436 (100%, M$^+$2-H$_2$O)

2) Synthesis of 2β-(4-Hydroxybutyl)-1α,3β-dihydroxy-9,10-secocholesta-5,7,10(19)-triene:

In 300 ml of THF was dissolved 18 mg of 2β-(4-hydroxybutyl)-1α,3β-dihydroxy-5,7-cholestadiene, and the solution was irradiated with light of a 400 W high-pressure mercury lamp through a Vycor filter for 25 seconds while bubbling argon gas through the solution under ice-cooling. Subsequently, the solution was heated under reflux for 1 hour in a nitrogen atmosphere to remove the solvent. The resultant residue was subjected to silica gel flash column chromatography using a 9:1 mixture of methylene chloride and ethanol as an eluent to obtain 5.3 mg (29%) of the title compound.

$^1$H-NMR (CDCl$_3$)δ: 0.55(3H,s), 0.85(3H,s), 0.88(3H,s), 5.00(1H,s), 5.38(1H,s), 6.01(1H,d,J=11.6 Hz), 6.34(1H,d,J=11.6 Hz)
UV λ$_{max}$ (EtOH) nm: 263
UV λ$_{min}$ (EtOH) nm: 228

EXAMPLE 3

Synthesis of 1α,3β-Dihydroxy-2β-(6-hydroxyhexyl)-9,10-secocholesta-5,7,10(19)-triene 1) Synthesis of 1α,3β-Dihydroxy-2β-(6-hydroxyhexyl)-cholesta-5,7-diene:

A solution of 1.51 g (11.0 mmol) of 6-chloro-1-hexanol in 5 ml of THF was slowly added dropwise to a suspension of 12.9 mmol ethylmagnesium bromide (in 4.3 ml of diethyl ether solution at a concentration of 3 mol/l) in 5 ml THF at −45° to −55° C. in an argon atmosphere, followed by stirring at −15° to −45° C. for 20 minutes and then at room temperature for 20 minutes. To the reaction mixture was added 271 mg (11.2 mmol) of magnesium, and the mixture was heated under reflux for 17 hours. After allowing the mixture to cool, a solution in 4.5 ml THF of 150 mg (261 μmol) of 1α,2α-epoxy-5α,8α-(3,5-dioxo-4-phenyl-1,2,4-triazolidino)-6-cholesten-3β-ol was added thereto dropwise over a period of 5 minutes, followed by heat-refluxing for 1.5 hours. The reaction mixture was poured into a saturated aqueous solution of ammonium chloride, filtered using Hyflo Super-Cell, and extracted with ethyl acetate. The extract was washed with a saturated aqueous solution of sodium chloride, dried over anhydrous magnesium sulfate, and distilled under reduced pressure to remove the solvent. The residue was roughly purified by fractional thin layer chromatography on silica gel using a 12:100 mixture of ethanol/dichloromethane as a developing solution and further purified by flash column chromatography on silica gel using a 6:1 mixture of ethyl acetate and n-hexane to obtain 87 mg (66%) of the title compound as white powder.

$^1$H-NMR (CDCl$_3$)δ: 0.62(3H,s), 0.87(6H,d,J=6.6 Hz), 0.94 (3H,d,J=6.1 Hz), 0.98(3H,s), 3.41(2H,t,J=6.6 Hz), 3.73(1H, brs), 4.08–4.21(1H,m), 5.28–5.36(1H,m), 5.63(1H,brd,J=4.9 Hz)

IR (neat, cm$^{-1}$): 3330 (br), 2945, 2870
UV $\lambda_{max}$ (EtOH) nm: 293, 282, 271
MS m/z : 500 (M$^+$), 43 (100%)

2) Synthesis of 1α,3β-Dihydroxy-2β-(6-hydroxyhexyl)-9,10-secocholesta-5,7,10(19)-triene:

In 200 ml of ethanol was dissolved 47.1 mg (94.1 μmol) of 1α,3β-dihydroxy-2β-(6-hydroxyhexyl)-cholesta-5,7-diene, and the solution was irradiated with light of a 400 W high-pressure mercury lamp through a Vycor filter for 3 minutes and 45 seconds while bubbling argon gas through the solution under ice-cooling. Subsequently, the solution was heated under reflux for 2 hours. The solvent was removed by distillation under reduced pressure, and the resultant residue was purified by fractional thin layer chromatography on silica gel using a 5:1 mixture of ethyl acetate and n-hexane to obtain 11.1 mg (24%) of the title compound as white powder.

$^1$H-NMR (CDCl$_3$)δ: 0.55(3H,s), 0.87(6H,d,J=6.6 Hz), 0.92 (3H,d,J=6.1 Hz), 3.64(2H,t,J=6.6 Hz), 4.04(1H,brd,J=7.8 Hz), 4.15(1H,brs), 5.01(1H,s), 5.37(1H,s), 6.03(1H,d,J=10.8 Hz), 6.34(1H,d,J=10.8 Hz)
IR (neat, cm$^{-1}$): 3345 (br), 2920, 2855
UV $\lambda_{max}$ (EtOH) nm: 263
UV $\lambda_{min}$ (EtOH) nm: 229
MS m/Z : 500 (M$^+$), 43 (100%)

EXAMPLE 4

Synthesis of 2β-(6-Hydroxyhexyl)-1α,3β,25-trihydroxy-9,10-secocholesta-5,7,10(19)-triene 1) Synthesis of 2β-(6-Hydroxyhexyl)-1α,3β,25-trihydroxycholesta-5,7-diene:

A solution of 1.51 g (11.0 mmol) of 6-chloro-1-hexanol in 5 ml of THF was slowly added dropwise to a suspension of 12.9 mmol ethylmagnesium bromide (in 4.3 ml of diethyl ether at a concentration of 3 mol/l) in 5 ml THF at −20° C. or lower in an argon atmosphere, followed by stirring at that temperature for 15 minutes and then at room temperature for 15 minutes. To the reaction mixture was added 271 mg (11.2 mmol) of magnesium, and the mixture was heated under reflux for 14 hours. After allowing the mixture to cool, a solution in 5 ml THF of 100 mg (170 μmol) of 1α,2α-epoxy-5α,8α-(3,5-dioxo-4-phenyl-1,2,4-triazolidino)-6-cholesten-3β,25-diol was slowly added thereto dropwise, followed by heat-refluxing for 2 hours. The reaction mixture was poured into a saturated aqueous solution of ammonium chloride, filtered using Hyflo Super-Cell, and extracted with ethyl acetate. The extract was washed with a saturated aqueous solution of sodium chloride, dried over anhydrous magnesium sulfate, and distilled under reduced pressure to remove the solvent. The resultant residue was roughly purified by flash column chromatography on silica gel using a 5:1 mixture of ethyl acetate and n-hexane and further purified by fractional thin layer chromatography on silica gel developing twice with a 13:100 mixture of ethanol and dichloromethane to obtain 41 mg (47%) of the title compound as a colorless oily substance.

$^1$H-NMR (CDCl$_3$)δ: 0.62(3H,s), 0.96(3H,d,J=6.6 Hz), 0.99 (3H,s), 1.21(6H,s), 3.61(2H,t,J=6.3 Hz), 3.75(1H,brs), 4.09–4.23(1H,m), 5.29–5.37(1H,m), 5.65(1H,brd,J=5.1 Hz)
IR (neat, cm$^{-1}$): 3355 (br), 2935, 2860
UV $\lambda_{max}$ (EtOH) nm: 294, 282, 272
MS m/z : 516 (M$^+$), 43 (100%)

2) Synthesis of 2β-(6-Hydroxyhexyl)-1α,3β-25-trihydroxy-9,10-secocholesta-5,7,10(19)-triene:

In 200 ml of ethanol was dissolved 36.8 mg (71.2 μmol) of 2β-(6-hydroxyhexyl)-1α,3β,25-trihydroxycholesta-5,7-diene, and the solution was irradiated with light of a 400 W high-pressure mercury lamp through a Vycor filter for 3 minutes and 10 seconds while bubbling argon gas through the solution under ice-cooling. Subsequently, the solution was heated under reflux for 2.5 hours. The solvent was removed by distillation under reduced pressure, and the resultant residue was purified by fractional thin layer chromatography on silica gel using a 7:1 mixed solvent of ethyl acetate and n-hexane to obtain 7.9 mg (21%) of the title compound as white powder.

$^1$H-NMR (CDCl$_3$)δ: 0.55(3H,s), 0.94(3H,d,J=6.1 Hz), 1.22 (6H,s), 3.64(2H,t,J=6.6 Hz), 3.99–4.09(1H,m), 4.15(1H, brs), 5.02(1H,s), 5.37(1H,s), 6.03(1H,d,J=10.7 Hz), 6.34 (1H,d,J=10.7 Hz)
IR (neat, cm$^{-1}$): 3410 (br), 2970, 2865
UV $\mu_{max}$ (EtOH) nm: 262
UV $\mu_{min}$ (EtOH) nm: 228
MS m/z : 516 (M$^+$), 59 (100%)

EXAMPLE 5

Synthesis of 2β-(4-Hydroxybutyl)-1α,3β,25-trihydroxy-9,10-secocholesta-5,7,10(19)-triene 1) Synthesis of 2β-(4-Hydroxybutyl)-1α,3β,25-trihydroxycholesta-5,7-diene:

A solution of 1.20 g (11.0 mmol) of 4-chloro-1-butanol in 5 ml of THF was slowly added dropwise to a suspension of 12.9 mmol ethylmagnesium bromide (in 4.3 ml of diethyl ether solution at a concentration of 3 mol/l) in 15 ml THF at −35° to −45° C. in an argon atmosphere over 20 minutes, followed by stirring at −20° C. or lower for 15 minutes and then at room temperature for 30 minutes. To the reaction mixture was added 271 mg (11.2 mmol) of magnesium, and the mixture was heated under reflux for 13.5 hours. After allowing the mixture to cool, a solution in 5 ml THF of 100 mg (170 μmol) of 1α,2α-epoxy-5α,8α-(3,5-dioxo-4-phenyl-1,2,4-triazolidino)-6-cholesten-3β,25-diol was added thereto dropwise over 10 minutes, followed by heat-refluxing for 2 hours. The reaction mixture was poured into a saturated aqueous solution of ammonium chloride, filtered using Hyflo Super-Cell, and extracted with ethyl acetate. The extract was washed with a saturated aqueous solution of sodium chloride, dried over anhydrous magnesium sulfate, and distilled under reduced pressure to remove the solvent. The resultant residue was roughly purified by flash column chromatography on silica gel using a 1:50 mixture of ethanol and ethyl acetate and further purified by fractional thin layer chromatography on silica gel using a 15:100 mixture of ethanol and dichloromethane to obtain 27 mg (33%) of the title compound as white powder.

$^1$H-NMR (DMSO-d$_6$+CDCl$_3$)δ: 0.62(3H,s), 0.95(3H,d,J= 6.3 Hz), 0.99(3H,s), 1.20(6H,s), 3.46(2H,t,J=6.1 Hz), 3.72 (1H,brs), 4.11–4.26(1H,m), 5.28–5.35(1H,m), 5.57–5.64 (1H,m)
IR (neat, cm$^{-1}$): 3390 (br), 2945, 2875
UV $\lambda_{max}$ (EtOH) nm: 294, 282, 272
MS m/z : 488 (M$^+$), 59 (100%)

2) Synthesis of 2β-(4-Hydroxybutyl)-1α,3β,25-trihydroxy-9,10-secocholesta-5,7,10(19)-triene:

In 200 ml of ethanol was dissolved 16.7 mg (34.2 μmol) of 2β-(4-hydroxybutyl)-1α,3β,25-trihydroxycholesta-5,7-diene, and the solution was irradiated with light of a 400 W high-pressure mercury lamp through a Vycor filter for 2 minutes while bubbling argon gas through the solution under ice-cooling. Subsequently, the solution was heated under reflux for 2 hours. The solvent was removed by distillation under reduced pressure, and the resultant residue was roughly purified by fractional thin layer chromatography on silica gel using a 1:7 mixed solvent of ethanol and dichloromethane and further purified by fractional thin layer chromatography on silica gel using a 1:100 mixture of ethanol and ethyl acetate to obtain 4.0 mg (24%) of the title compound as white powder.

$^1$H-NMR (CDCl$_3$)δ: 0.55(3H,s), 0.94(3H,d,J=5.9 Hz), 1.22 (6H,s), 3.68(2H,t,J=6.1 Hz), 4.01–4.12(1H,m), 4.16(1H, brs), 5.02(1H,s), 5.37(1H,s), 6.03(1H,d,J=11.3 Hz), 6.34 (1H,d,J=11.3 Hz)
IR (neat, cm$^{-1}$): 3385 (br), 2945, 2875
UV λ$_{max}$ (EtOH) nm: 264
UV λ$_{min}$ (EtOH) nm: 229
MS m/z : 488 (M$^+$), 133 (100%)

EXAMPLE 6

Synthesis of 2β-Methyl-1α,3β,25-trihydroxy-9,10-secocholesta-5,7,10(19)-triene

1) Synthesis of 2β-Methyl-1α,3β-25-trihydroxycholesta-5,7-diene:

A solution of 100 mg (170 μmol) of 1α,2α-epoxy-5α,8α-(3,5-dioxo-4-phenyl-1,2,4-triazolidino)-6-cholesten-3β,25-diol in 3 ml of THF was added to 2 ml (2.0 mmol) of a THF solution of methylmagnesium bromide (1 mol/l), followed by heating under reflux for 2 hours in an argon atmosphere. After allowing the solution to cool, the reaction mixture was poured into a saturated aqueous solution of ammonium chloride, filtered using Hyflo Super-Cell, and extracted with ethyl acetate. The extract was washed with a saturated aqueous solution of sodium chloride, dried over anhydrous magnesium sulfate, and distilled under reduced pressure to remove the solvent. The resultant residue was roughly purified by fractional thin layer chromatography on silica gel using a 9:1 mixture of ethyl acetate and n-hexane and further purified by fractional thin layer chromatography on silica gel using a 12:100 mixture of ethanol and dichloromethane to obtain 17 mg (23%) of the title compound as white powder.
$^1$H-NMR (CDCl$_3$)δ: 0.63(3H,s), 0.96(3H,d,J=6.3 Hz), 1.01 (3H,s), 1.11(3H,d,J=7.8 Hz), 1.22(6H,s), 3.67(1H,brs), 4.06–4.25(1H,m), 5.33–5.43(1H,m), 5.66–5.73(1H,m)
IR (neat, cm$^{-1}$): 3380 (br), 2940, 2905
UV λ$_{max}$ (EtOH) nm: 293, 282, 272
MS m/z : 430 (M$^+$), 59 (100%)

2) Synthesis of 2β-Methyl-1α,3β,25-trihydroxy-9,10-secocholesta-5,7,10(19)-triene:

In 200 ml of ethanol was dissolved 17.2 mg (39.9 μmol) of 2β-methyl-1α,3β,25-trihydroxycholesta-5,7-diene, and the solution was irradiated with light of a 400 W high-pressure mercury lamp/Vycor filter for 2 minutes while bubbling argon gas through the solution under ice-cooling. Subsequently, the solution was heated under reflux for 2 hours. The solvent was removed by distillation under reduced pressure, and the resultant residue was purified by fractional thin layer chromatography on silica gel using a 5:1 mixture of ethyl acetate and n-hexane to obtain 4.1 mg (24%) of the title compound as white foam.
$^1$H-NMR (CDCl$_3$)δ: 0.55(3H,s), 0.94(3H,d,J=6.1 Hz), 1.15 (3H,d,J=6.8 Hz), 1.22(6H,s), 3.95–4.03(1H,m), 4.04(1H, brs), 5.02(1H,s), 5.37(1H,s), 6.03(1H,d,J=11.7 Hz), 6.35 (1H,d,J=11.7 Hz)
IR (neat, cm$^{-1}$): 3375 (br), 2930, 2870
UV λ$_{max}$ (EtOH) nm: 264
UV λ$_{min}$ (EtOH) nm: 228
MS m/z : 430 (M$^+$), 59 (100%)

EXAMPLE 7

Synthesis of 1α,3β-Dihydroxy-2β-methyl-9,10-secocholesta-5,7,10(19)-triene

1) Synthesis of 1α,3β-Dihydroxy-2β-methylcholesta-5,7-diene:

A solution of 100 mg (174 μmol) of 1α,2α-epoxy-5α,8α-(3,5-dioxo-4-phenyl-1,2,4-triazolidino)-6-cholesten-3β-ol in 4 ml of THF was added to 2 ml (containing 2.0 mmol methylmagnesium bromide) of solution of methylmagnesium bromide (1 mol/l) in THF, followed by heating under reflux for 2 hours in an argon atmosphere. After allowing the solution to cool, the reaction mixture was poured into a saturated aqueous solution of ammonium chloride, filtered using Hyflo Super-Cell, and extracted with ethyl acetate. The extract was washed with a saturated aqueous solution of sodium chloride, dried over anhydrous magnesium sulfate, and distilled under reduced pressure to remove the solvent. The residue was purified by fractional thin layer chromatography on silica gel using a 3:1 mixture of ethyl acetate and n-hexane to obtain 17 mg (24%) of the title compound as pale yellow powder.
$^1$H-NMR (CDCl$_3$)δ: 0.62(3H,s), 0.87(6H,d,J=6.6 Hz), 0.94 (3H,d,J=6.3 Hz), 1.00(3H,s), 1.10(3H,d,J=7.9 Hz), 3.65(1H, brs), 4.13–4.26(1H,m), 5.32–5.41(1H,m), 5.69(1H,brd,J= 5.6 Hz)
IR (neat, cm$^{-1}$): 3345 (br), 2945, 2870
UV λ$_{max}$ (EtOH) nm: 293, 282, 271
MS m/z : 414 (M$^+$), 43 (100%)

2) Synthesis of 1α,3β-Dihydroxy-2β-methyl-9,10-secocholesta-5,7,10(19)-triene:

In 200 ml of ethanol was dissolved 13.0 mg (31.4 μmol) of 1α,3β-dihydroxy-2β-methylcholesta-5,7-diene, and the solution was irradiated with light using a 400 W high-pressure mercury lamp/Vycor filter for 1 minute and 55 seconds while bubbling argon gas through the solution under ice-cooling. Subsequently, the solution was heated under reflux for 2 hours. The solvent was removed by distillation under reduced pressure, and the resultant residue was purified by fractional thin layer chromatography on silica gel using a 2:1 mixture of ethyl acetate and n-hexane to obtain 3.6 mg (28%) of the title compound as a colorless oily substance.
$^1$H-NMR (CDCl$_3$)δ: 0.55(3H,s), 0.87(6H,d,J=6.6 Hz), 0.92 (3H,d,J=5.9 Hz), 1.15(3H,d,J=6.8 Hz), 3.95–4.02(1H,m), 4.03(1H,brs), 5.02(1H,s), 5.37(1H,s), 6.03(1H,d,J=11.7 Hz), 6.35(1H,d,J=11.7 Hz)
IR (neat, cm$^{-1}$): 3390 (br), 2945, 2930, 2870
UV λ$_{max}$ (EtOH) nm: 262
UV λ$_{min}$ (EtOH) nm: 227
MS m/Z : 414 (M$^+$), 148 (100%)

EXAMPLE 8

Synthesis of 2β-Ethyl-1α,3β-25-trihydroxy-9,10-secocholesta-5,7,10(19)-triene

1) Synthesis of 2β-Ethyl-1α,3β,25-trihydroxycholesta-5,7-diene:

To 5 ml of THF was added 2.4 ml of a THF solution of ethylmagnesium bromide at a concentration of 1.04 mol/l in an argon atmosphere, and a solution of 100 mg of 1α,2α-epoxy-5α,8α-(3,5-dioxo-4-phenyl-1,2,4-triazolidino)-6-cholesten-3β,25-diol in 5 ml of THF was then added to the solution, followed by heat-refluxing for 2.5 hours. Water was added to the reaction mixture, and the mixture was extracted with ethyl acetate. The extract was washed with a saturated aqueous solution of sodium chloride, dried over anhydrous magnesium sulfate, and distilled under reduced pressure to remove the solvent. The resultant residue was purified by fractional thin layer chromatography on silica gel using a 10:1 mixture of dichloromethane and ethanol to obtain 22.7 mg (30%) of the title compound as a colorless oily substance.
$^1$H-NMR (CDCl$_3$)δ: 0.63(3H,s), 0.96(3H,d,J=6.6 Hz), 1.01 (3H,s), 1.05(3H,t,J=7.4 Hz), 1.22(6H,s), 3.80(1H,brs), 4.13–4.27(1H,m), 5.30–5.40(1H,m), 5.68(1H,brd,J=4.3 Hz)

IR (neat, cm$^{-1}$): 3400 (br), 2955, 2870
UV $\lambda_{max}$ (EtOH) nm: 283, 272
MS m/z : 444 (M$^+$), 59 (100%)

2) Synthesis of 2β-Ethyl-1α,3β,25-trihydroxy-9,10-secocholesta-5,7,10(19)-triene:

In 200 ml of ethanol was dissolved 22.7 mg of 2p-ethyl-1α,3β,25-trihydroxycholesta-5,7-diene, and the solution was irradiated with light using a 400 W high-pressure mercury lamp/Vycor filter for 110 seconds while bubbling argon gas through the solution under ice-cooling. Subsequently, the solution was heated under reflux for 3 hours. The solvent was removed by distillation under reduced pressure, and the resultant residue was purified by fractional thin layer chromatography on silica gel using a 20:1 mixture of dichloromethane and ethanol to obtain 3.56 mg (16%) of the title compound.

$^1$H-NMR (CDCl$_3$)δ: 0.55(3H,s), 0.94(3H,d,J=6.3 Hz), 0.99 (3H,t,J=7.0 Hz), 1.22(6H,s), 4.00–4.10(1H,m), 4.17(1H, brs), 5.02(1H,s), 5.38(1H,s), 6.04(1H,d,J=11.0 Hz), 6.34 (1H,d,J=11.0 Hz)
IR (neat, cm$^{-1}$): 3410 (br), 2940, 2870
UV $\lambda_{max}$ (EtOH) nm: 263
UV $\lambda_{min}$ (EtOH) nm: 228
MS m/z : 444 (M$^+$), 133 (100%)

EXAMPLE 9

Synthesis of 1α,3β-Dihydroxy-2β-(4-pentenyl)-9,10-secocholesta-5,7,10(19)-triene 1) Synthesis of 1α,3β-Dihydroxy-2β-(4-pentenyl)cholesta-5,7-diene:

To 5 ml of THF was added 122 mg of magnesium in an argon atmosphere, and then 595 μl of 5-bromo-1-pentene and a small amount of iodine were added thereto, followed by stirring at room temperature for 2.5 hours. To the reaction mixture was added a THF (2 ml) solution of 100 mg of 1α,2α-epoxy-3β-hydroxy-5,7-cholestadiene, followed by heat-refluxing for 2 hours in an argon atmosphere. A saturated aqueous solution of ammonium chloride was added to the reaction mixture, and the mixture was extracted with ethyl acetate. The extract was washed with a saturated aqueous solution of sodium chloride, dried over anhydrous magnesium sulfate, and distilled under reduced pressure to remove the solvent. The resultant residue was purified by fractional thin layer chromatography on silica gel using a 1:1 mixture of ethyl acetate and n-hexane to obtain 67.4 mg (59%) of the title compound as a colorless oily substance.

$^1$H-NMR (CDCl$_3$)δ: 0.62(3H,s), 0.87(6H,d,J=6.6 Hz), 0.94 (3H,d,J=6.3 Hz), 1.00(3H,s), 3.76(1H,brs), 4.07–4.21(1H, m), 4.85–5.01(2H,m), 5.30–5.40(1H,m), 5.60–5.69(1H,m), 5.70–5.95(1H,m)
IR (neat, cm$^{-1}$): 3480 (br), 2970, 2880
UV $\lambda_{max}$ (EtOH) nm: 293, 282, 271
MS m/z : 468 (M$^+$), 55 (100%)

2) Synthesis of 1α,3β-Dihydroxy-2β-(4-pentenyl)-9,10-secocholesta-5,7,10(19)-triene:

In 200 ml of ethanol was dissolved 20 mg of 1α,3β-dihydroxy-2β-(4-pentenyl)cholesta-5,7-diene, and the solution was irradiated with light using a 400 W high-pressure mercury lamp/Vycor filter for 110 seconds while bubbling argon gas through the solution under ice-cooling. Subsequently, the solution was heated under reflux for 2.5 hours. The solvent was removed by distillation under reduced pressure, and the resultant residue was purified by fractional thin layer chromatography on silica gel using a 1:1 mixture of ethyl acetate and n-hexane to obtain 5.06 mg (25.3%) of the title compound.

$^1$H-NMR (CDCl$_3$)δ: 0.55(3H,s), 0.87(6H,d,J=6.6 Hz), 0.92 (3H,d,J=5.8 Hz), 4.04–4.13(1H,m), 4.15(1H,brs), 4.88–5.08 (3H,m), 5.37(1H,s), 5.70–5.94(1H,m), 6.03(1H,d,J=11.0 Hz), 6.35(1H,d,J=11.0 Hz)
IR (neat, cm$^{-1}$): 3480, 2950, 2930, 2880
UV $\lambda_{max}$ (EtOH) nm: 263
UV $\lambda_{min}$ (EtOH) nm: 229
MS m/z : 468 (M$^+$), 147 (100%)

EXAMPLE 10

Synthesis of 2β-(4-Pentenyl)-1α,3β,25-trihydroxy-9,10-secocholesta-5,7,10(19)-triene 1) Synthesis of 2β-(4-Pentenyl)-1α,3β,25-trihydroxycholesta-5,7-diene:

To 5 ml of THF was added 146 mg of magnesium in an argon atmosphere, and then 713 μl of 5-bromo-1-pentene and a small amount of iodine were added thereto, followed by stirring at room temperature for 2 hours. To the reaction mixture was added a THF (5 ml) solution of 100 mg of 3β,25-dihydroxy-1α,2α-epoxy-5,7-cholestadiene, followed by heat-refluxing for 2 hours in an argon atmosphere. A saturated aqueous solution of ammonium chloride was added to the reaction mixture, and the mixture was extracted with ethyl acetate. The extract was washed with a saturated aqueous solution of sodium chloride, dried over anhydrous magnesium sulfate, and distilled under reduced pressure to remove the solvent. The resultant residue was purified by fractional thin layer chromatography on silica gel using a 20:1 mixture of dichloromethane and ethanol to obtain 32.8 mg (28%) of the title compound as a colorless oily substance.

$^1$H-NMR (CDCl$_3$)δ: 0.62(3H,s), 0.96(3H,d,J=6.3 Hz), 1.01 (3H,s), 1.22(6H,s), 3.76(1H,brs), 4.17–4.18(1H,m), 4.92–5.08(2H,m), 5.31–5.39(1H,m), 5.65–5.72(1H,m), 5.74–5.91(1H,m)
IR (neat, cm$^{-1}$): 3400 (br), 2940, 2870
UV $\lambda_{max}$ (EtOH) nm: 294, 281, 271
MS m/z : 485 (M$^+$), 55 (100%)

2) Synthesis of 2β-(4-Pentenyl)-1α,3β,25-trihydroxy-9,10-secocholesta-5,7,10(19)-triene:

In 200 ml of ethanol was dissolved 32.8 mg of 2β-(4-pentenyl)-1α,3β,25-trihydroxycholesta-5,7-diene, and the solution was irradiated with light using a 400 W high-pressure mercury lamp/Vycor filter for 150 seconds while bubbling argon gas through the solution under ice-cooling. Subsequently, the solution was heated under reflux for 3 hours. The solvent was removed by distillation under reduced pressure, and the resultant residue was purified by fractional thin layer chromatography on silica gel using a 20:1 mixture of dichloromethane and ethanol to obtain 8.08 mg (25%) of the title compound.

$^1$H-NMR (CDCl$_3$)δ: 0.55(3H,s), 0.94(3H,d,J=6.3 Hz), 1.22 (6H,s), 4.01–4.10(1H,m), 4.16(1H,brs), 4.91–5.09(3H,m), 5.37(1H,s), 5.75–5.92(1H,m), 6.03(1H,d,J=11.2 Hz), 6.34 (1H,d,J=11.2 Hz)
IR (neat, cm$^{-1}$): 3400 (br), 2950, 2980
UV $\lambda_{max}$ (EtOH) nm: 263
UV $\lambda_{min}$ (EtOH) nm: 228
MS m/z : 485 (M$^+$), 133 (100%)

EXAMPLE 11

Synthesis of 2β-Butyl-1α,3β-dihydroxy-9,10-secocholesta-5,7,10(19)-triene

1) Synthesis of 2β-Butyl-1α,3β-dihydroxycholesta-5,7-diene:

To 5 ml of THF cooled to −70° C. was added 808 μl of a 1.61 mol/l solution of n-butyl lithium in hexane in an argon atmosphere. After stirring at that temperature for a while, a solution of 100 mg of 1α,2α-epoxy-3β-hydroxy-5,7-cholestadiene in 10 ml of THF was added to the solution at −70° C. Then, 57.5 μl of tri(fluoro)etherboron was added thereto, followed by stirring at −70° C. for 20 minutes and then under cooling with ice for 30 minutes. A saturated aqueous solution of ammonium chloride was poured into the reaction mixture, and the reaction mixture was extracted with ethyl acetate. The extract was washed with a saturated aqueous solution of sodium chloride and dried over anhydrous magnesium sulfate. The solvent was removed by distillation under reduced pressure, and the resultant residue was purified by fractional thin layer chromatography on silica gel using a 35:1 mixture of dichloromethane and ethanol to obtain 14 mg (12%) of the title compound as a colorless oily substance.

$^1$H-NMR (CDCl$_3$)δ: 0.62(3H,s), 0.87(6H,d,J=6.6 Hz), 0.90–0.95(6H,m), 1.02(3H,s), 3.78(1H,brs), 4.13–4.27(1H, m), 5.32–5.40(1H,m), 5.62–5.71(1H,m)
IR (neat, cm$^{-1}$): 3400 (br), 2950, 2930, 2870
UV λ$_{max}$ (EtOH) nm: 294, 282, 271
MS m/z : 456 (M$^+$), 55 (100%)

2) Synthesis of 2β-Butyl-1α,3β-dihydroxy-9,10-secocholesta-5,7,10(19)-triene:

In 200 ml of ethanol was dissolved 14 mg of 2β-butyl-1α,3β-dihydroxycholesta-5,7-diene, and the solution was irradiated with light using a 400 W high-pressure mercury lamp/Vycor filter for 80 seconds and then for 40 seconds while bubbling argon gas through the solution under ice-cooling, followed by heating under reflux for 3 hours. The solvent was removed by distillation under reduced pressure, and the resultant residue was purified by fractional thin layer chromatography on silica gel using a 40:1 mixture of dichloromethane and ethanol to obtain 1.52 mg (11%) of the title compound.

$^1$H-NMR (CDCl$_3$)δ: 0.55(3H,s), 0.87(6H,d,J=6.6 Hz), 0.91–0.98(6H,m), 4.01–4.10(1H,m), 4.17(1H,brs), 5.02(1H, s), 5.37(1H,s), 6.03(1H,d,J=11.5 Hz), 6.34(1H,d,J=11.5 Hz)
IR (neat, cm$^{-1}$): 3400 (br), 2960, 2930, 2870
UV λ$_{max}$ (EtOH) nm: 263
UV λ$_{min}$ (EtOH) nm: 228
MS m/z : 456 (M$^+$), 57 (100%)

EXAMPLE 12

Synthesis of 2β-Butyl-1α,3β,25-trihydroxy-9,10-secocholesta-5,7,10(19)-triene

1) Synthesis of 2β-Butyl-1α,3β,25-trihydroxycholesta-5,7-diene:

To 5 ml of THF cooled to −70° C. was added 1.94 ml of a 1.61 mol/l solution of n-butyl lithium in hexane in an argon atmosphere. After stirring at that temperature for a while, a THF (5 ml) solution of 100 mg of 3β,25-dihydroxy-1α,2α-epoxy-5,7-cholestadiene was added to the solution at −70° C. Then, 55.2 μl of tri(fluoro)etherboron was added thereto, followed by stirring at −70° C. for 30 minutes and then under cooling with ice for 30 minutes. A saturated aqueous solution of ammonium chloride was poured into the reaction mixture, and the reaction mixture was extracted with ethyl acetate. The extract was washed with a saturated aqueous solution of sodium chloride and dried over anhydrous magnesium sulfate. The solvent was removed by distillation under reduced pressure, and the resultant residue was roughly purified by fractional thin layer chromatography on silica gel using a 10:1 mixture of dichloromethane and ethanol and further purified by fractional thin layer chromatography on silica gel using a 1:1 mixture of ethyl acetate and n-hexane to obtain 9.5 mg (8%) of the title compound as a colorless oily substance.

$^1$H-NMR (CDCl$_3$)δ: 0.63(3H,s), 0.89–0.98(6H,m), 1.02(3H, s), 1.22(6H,s), 3.78(1H,brs), 4.11–4.16(1H,m), 5.31–5.32 (1H,m), 5.65–5.74(1H,m)
IR (neat, cm$^{-1}$): 3400 (br), 2970, 2890
UV λ$_{max}$ (EtOH) nm: 294, 282, 271
MS m/z : 472 (M$^+$), 59 (100%)

2) Synthesis of 2β-Butyl-1α,3β,25-trihydroxy-9,10-secocholesta-5,7,10(19)-triene:

In 200 ml of ethanol was dissolved 9.5 mg of 2β-butyl-1α,3β,25-trihydroxycholesta-5,7-diene, and the solution was irradiated with light using a 400 W high-pressure mercury lamp/Vycor filter for 80 seconds while bubbling argon gas through the solution under ice-cooling, followed by heating under reflux for 3 hours. The solvent was removed by distillation under reduced pressure, and the resultant residue was purified by fractional thin layer chromatography on silica gel using a 1:1 mixture of ethyl acetate and n-hexane to obtain 1.36 mg (14%) of the title compound.

$^1$H-NMR (CDCl$_3$)δ: 0.55(3H,s), 0.92(3H,t,J=6.8 Hz), 0.94 (3H,d,J=6.3 Hz), 1.22(6H,s), 4.01–4.10(1H,m), 4.15(1H, brs), 5.02(1H,s), 5.38(1H,s), 6.04(1H,d,J=10.9 Hz), 6.35 (1H,d,J=10.9 Hz)
IR (neat, cm$^{-1}$): 3400 (br), 2930, 2880
UV λ$_{max}$ (EtOH) nm: 264
UV λ$_{min}$ (EtOH) nm: 228
MS m/z : 472 (M$^+$), 55 (100%)

EXAMPLE 13

Synthesis of 1α,3β-Dihydroxy-2β-pentyl-9,10-secocholesta-5,7,10(19)-triene

1) Synthesis of 1α,3β-Dihydroxy-2β-pentylcholesta-5,7-diene:

To 5 ml of THF were added 127 mg of magnesium and a small amount of iodine in an argon atmosphere, followed by stirring until the color of the iodine disappeared. To the solution was added 674 μl of 1-bromopentene, followed by stirring at room temperature for 1.5 hours. To the reaction mixture was added a THF (5 ml) solution of 100 mg of 1α,2α-epoxy-5α,8α-(3,5-dioxo-4-phenyl-1,2,4-triazolidino)-6-cholesten-3β-ol, followed by heat-refluxing for 2 hours. A saturated aqueous solution of ammonium chloride was poured into the reaction mixture, and the mixture was extracted with ethyl acetate. The extract was washed with a saturated aqueous solution of sodium chloride, dried over anhydrous magnesium sulfate, and distilled under reduced pressure to remove the solvent. The resultant residue was roughly purified by fractional thin layer chromatography on silica gel using a 20:1 mixture of dichloromethane and ethanol and further purified by fractional thin layer chromatography on silica gel using a 1:2 mixture of ethyl acetate and n-hexane to obtain 18.8 mg (23%) of the title compound as a colorless oily substance.

$^1$H-NMR (CDCl$_3$)δ: 0.62(3H,s), 0.87(6H,d,J=6.6 Hz), 0.94 (3H,d,J=6.3 Hz), 1.01(3H,s), 3.77(1H,brs), 4.10–4.22(1H, m), 5.32–5.40(1H,m), 5.67(1H,brd,J=5.6 Hz)
IR (neat, cm$^{-1}$): 3400 (br), 2940, 2920, 2870
UV λ$_{max}$ (EtOH) nm: 292, 282, 271
MS m/z : 470 (M$^+$), 55 (100%)

2) Synthesis of 1α,3β-Dihydroxy-2β-pentyl-9,10-secocholesta-5,7,10(19)-triene:

In 200 ml of ethanol was dissolved 18.8 mg of 1α,3β-dihydroxy-2β-pentylcholesta-5,7-diene, and the solution was irradiated with light using a 400 W high-pressure mercury lamp/Vycor filter for 110 seconds while bubbling argon gas through the solution under ice-cooling. Subsequently, the solution was heated under reflux for 3 hours. The solvent was removed by distillation under reduced pressure, and the resultant residue was roughly purified by fractional thin layer chromatography on silica gel using a 1:3 mixture of ethyl acetate and n-hexane and further purified by fractional thin layer chromatography on silica gel using a 1:3 mixture of ethyl acetate and n-hexane to obtain 3.38 mg (18%) of the title compound.

¹H-NMR (CDCl₃)δ: 0.55(3H,s), 0.87(6H,d,J=6.6 Hz), 0.92 (3H,d,J=6.0 Hz), 4.01–4.10(1H,m), 4.15(1H,brs), 5.02(1H, s), 5.37(1H,s), 6.03(1H,d,J=11.1 Hz), 6.34(1H,d,J=11.1 Hz)
IR (neat, cm⁻¹): 3400 (br), 2960, 2940, 2880
UV λ$_{max}$ (EtOH) nm: 264
UV λ$_{min}$ (EtOH) nm: 228
MS m/z : 470 (M⁺), 133 (100%)

EXAMPLE 14

Synthesis of 2β-(3-Hydroxypropyl)-1α,3β-25-trihydroxy-9,10-secocholesta-5,7,10(19)-triene 1) Synthesis of 2β-(2-Propenyl)-1α,3β,25-trihydroxycholesta-5,7-diene:

To a THF (30 ml) solution of 1.53 g (12.4 mmol) of 3-bromo-1-pentene was added 302 mg (12.4 mmol) of magnesium, and the mixture was heated under reflux for 1.5 hours. After allowing the solution to cool, a THF (5 ml) solution of 101 mg (0.24 mmol) of 3β,25-dihydroxy-1α,2α-epoxy-cholesta-5,7-diene was slowly added thereto dropwise, followed by heat-refluxing for 13 hours. The reaction mixture was poured into a saturated aqueous solution of ammonium chloride and extracted with ethyl acetate. The extract was washed with a saturated aqueous solution of sodium chloride and dried over magnesium sulfate. The solvent was removed by distillation, and the resultant residue was purified by fractional thin layer chromatography on silica gel developing twice with a 5:0.3 mixture of dichloromethane and ethanol to obtain 92 mg (83%) of the title compound as a colorless oily substance.

¹H-NMR (CDCl₃)δ: 0.62(3H,s), 0.95(3H,d,J=6.3 Hz), 1.02 (3H,s), 1.21(6H,s), 3.74(1H,brs), 4.13–4.26(1H,m), 4.95–5.15(2H,m), 5.30–5.39(1H,m), 5.67(1H,brs,J=6.3 Hz), 5.70–5.99(1H,m)
IR (neat, cm⁻¹): 3375 (br), 2940, 2875, 1380, 1040, 905
UV λ$_{max}$ (EtOH) nm: 293, 282, 272
MS m/z : 456 (M⁺), 59 (100%)

2) Synthesis of 2β-(2-Propenyl)-1α,3β,25-tris(triethylsilyloxy)cholesta-5,7-diene:

To a solution of 31.5 mg (0.069 mmol) of 2β-(2-propenyl)-1α,3β,25-trihydroxycholesta-5,7-diene and 373 mg (6.21 mmol) of imidazole in 2 ml of 1,3-dimethyl-2-imidazolidinone (DMI) was added dropwise 173 μl (1.03 mmol) of chlorotriethylsilane (TESCl), and the mixture was stirred at room temperature for 5.5 hours. The reaction mixture was poured into a saturated aqueous solution of sodium chloride and extracted with n-hexane. The extract was washed with water and dried over magnesium sulfate. The solvent was removed by distillation, and the resultant residue was purified by fractional thin layer chromatography on silica gel using a 10:1 mixture of n-hexane and ethyl acetate to obtain 29 mg (53%) of the title compound as a colorless oily substance.

¹H-NMR (CDCl₃)δ: 0.48–0.70(21H,m), 0.87–1.05(33H,m), 1.19(6H,s), 3.80(1H,brs), 4.12–4.26(1H,m), 4.97(1H,brs), 5.04(1H,dd,J=1.2,7.3 Hz), 5.26–5.35(1H,m), 5.60(1H,brd, J=4.1 Hz), 5.67–5.97(1H,m)
IR (neat, cm⁻¹): 2950, 2870, 1455, 1375, 1230, 1085, 1000, 735, 715
UV λ$_{max}$ (EtOH) nm: 294, 282, 272
MS m/z : 798 (M⁺), 103 (100%)

3) Synthesis of 2β-(3-Hydroxypropyl)-1α,3β,25-tris(triethylsilyloxy)cholesta-5,7-diene:

To a solution of 29 mg (0.036 mmol) of the compound obtained in (2) above in 2 ml of THF was added 145 μl (0.145 mmol) of borine (BH₃) (1 mol/l in THF) in an argon atmosphere, followed by stirring at room temperature for 20 hours. To the reaction mixture were added successively 0.5 ml of 3M sodium hydroxide and 0.4 ml of hydrogen peroxide, followed by stirring for 30 minutes. The mixture was extracted with ethyl acetate, and the extract was washed with a saturated aqueous solution of sodium chloride and dried over magnesium sulfate. The solvent was removed by distillation, and the resultant residue was purified by fractional thin layer chromatography on silica gel using a 1:5 mixture of ethyl acetate and n-hexane to obtain 9.0 mg (30%) of the title compound as a colorless oily substance.

¹H-NMR (CDCl₃)δ: 0.49–0.71(21H,m), 0.85–1.04(33H,m), 1.19(6H,s), 3.65(2H,t,J=6.3 Hz), 3.75(1H,brs), 4.14–4.28 (1H,m), 5.26–5.35(1H,m), 5.59(1H,brd,J=5.1 Hz)
IR (neat, cm⁻¹): 3375 (br), 2955, 2880, 1460, 1240, 1090, 1050, 1010, 740, 725
UV λ$_{max}$ (EtOH) nm: 294, 282, 272
MS m/z : 816 (M⁺), 103 (100%)

4) Synthesis of 2β-(3-Hydroxypropyl)-1α,3β,25-trihydroxycholesta-5,7-diene:

To a solution of 9 mg (0.011 mmol) of the compound obtained in (3) above in 2 ml of THF was added 231 μl (0.231 mmol) of TBAF (1 mol/l in THF), followed by heating under reflux for 4 hours. A saturated aqueous solution of sodium hydrogen carbonate was added to the reaction mixture, and the reaction mixture was extracted with ethyl acetate. The extract was washed with a saturated aqueous solution of sodium hydrogen carbonate and dried over magnesium sulfate. The solvent was removed by distillation, and the resultant residue was purified by fractional thin layer chromatography on silica gel using a 5:1 mixture of dichloromethane and ethanol to obtain 5.0 mg (89%) of the title compound as white crystals.

¹H-NMR (CDCl₃)δ: 0.62(3H,s), 0.96(3H,d,J=6.1 Hz), 1.02 (3H,s), 1.22(6H,s), 3.69(2H,br), 3.75(1H,brs), 4.15–4.28 (1H,m), 5.31–5.41(1H,m), 5.63–5.72(1H,m)
IR (neat, cm⁻¹): 3390 (br), 2950, 2880, 1470, 1380, 1065, 760
UV λ$_{max}$ (EtOH) nm: 293, 282, 272
MS m/z : 474 (M⁺), 59 (100%)

5) Synthesis of 2β-(3-Hydroxypropyl)-1α,3β,25-trihydroxy-9,10-secocholesta-5,7,10(19)-triene:

In 200 ml of ethanol was dissolved 4.7 mg (0.010 mmol) of the compound obtained in (4) above, and the solution was irradiated with light using a 400 W high-pressure mercury lamp/Vycor filter for 90 seconds while bubbling argon gas through the solution under ice-cooling. Subsequently, the solution was heated under reflux for 2 hours in an argon atmosphere. The solvent was removed by distillation, and the resultant residue was purified by fractional thin layer chromatography on silica gel using a 5:1 mixture of dichloromethane and ethanol to obtain 1.1 mg (24%) of the title compound as white crystals.

¹H-NMR (CDCl₃)δ: 0.55(3H,s), 0.94(3H,d,J=6.1 Hz), 1.22 (6H,s), 3.70(2H,t,J=6.3 Hz), 4.02–4.10(1H,m), 4.17(1H, brs), 5.03(1H,s), 5.38(1H,s), 6.03(1H,d,J=11.7 Hz), 6.35 (1H,d,J=11.7 Hz)
UV λ$_{max}$ (EtOH) nm: 264
UV λ$_{min}$ (EtOH) nm: 228
MS m/z : 474 (M⁺), 59 (100%)

EXAMPLE 15

Synthesis of 2β-(5-Hydroxypentyl)-1α,3β,25-trihydroxy-9,10-secocholesta-5,7,10(19)-triene 1) Synthesis of 2β-(4-Pentenyl)-1α,3β,25-trihydroxycholesta-5,7-diene:

To a THF (3 ml) solution of 1.01 ml (8.5 mmol) of 5-bromo-1-pentene was added 207 mg (8.5 mmol) of magnesium, followed by stirring at room temperature for 2 hours. A THF (3 ml) solution of 101 mg (0.24 mmol) of 3β,25-dihydroxy-1α,2α-epoxycholesta-5,7-diene was slowly added thereto dropwise, followed by heat-refluxing for 3.5 hours. The reaction mixture was poured into a saturated aqueous solution of ammonium chloride and extracted with ethyl acetate. The extract was washed with water and dried over magnesium sulfate. The solvent was removed by distillation, and the resultant residue was purified by fractional thin layer chromatography on silica gel using a 10:1 mixture of dichloromethane and ethanol, and further purified by fractional thin layer chromatography on silica gel using a 20:1 mixture of dichloromethane and ethanol to obtain 50 mg (42%) of the title compound as a colorless oily substance while recovering 40 mg of the starting epoxide compound.

$^1$H-NMR (CDCl$_3$)δ: 0.62(3H,s), 0.96(3H,d,J=6.3 Hz), 1.01 (3H,s), 1.22(6H,s), 3.77(1H,brs), 4.16–4.26(1H,m), 4.92–5.08(2H,m), 5.33–5.39(1H,m), 5.64–5.70(1H,m), 5.73–5.90(1H,m)

IR (neat, cm$^{-1}$): 3375 (br), 2950, 2900, 2870, 1380, 1060, 910, 760

UV λ$_{max}$ (EtOH) nm: 294, 281, 271

MS m/z : 485 (M$^+$), 55 (100%)

2) Synthesis of 2β-(4-Pentenyl)-1α,3β,25-tris (triethylsilyloxy)cholesta-5,7-diene:

To a solution of 50 mg (0.103 mmol) of 2β-(4-pentenyl)-1α,3β,25-trihydroxycholesta-5,7-diene and 1.1 g (15.5 mmol) of imidazole in 3 ml of DMI was added dropwise 260 μl (1.55 mmol) of TESCl, and the mixture was stirred at room temperature for 48 hours. The reaction mixture was poured into a saturated aqueous solution of sodium chloride and extracted with n-hexane and ethyl acetate. The extract was washed with water and dried over magnesium sulfate. The solvent was removed by distillation, and the resultant residue was purified by fractional thin layer chromatography on silica gel using a 40:1 mixture of n-hexane and ethyl acetate to obtain 49 mg (58%) of the title compound as a colorless oily substance.

$^1$H-NMR (CDCl$_3$)δ: 0.50–0.70(21H,m), 0.88–1.00(33H,m), 1.19(6H,s), 3.87(1H,brs), 4.13–4.22(1H,m), 4.90–5.05(2H, m), 5.29–5.33(1H,m), 5.55–5.62(1H,m), 5.73–5.90(1H,m)

IR (neat, cm$^{-1}$): 2950, 2920, 2870, 1460, 1380, 1240, 1090, 1010, 820, 740, 730

UV λ$_{max}$ (EtOH) nm: 294, 282, 272

MS m/Z : 826 (M$^+$), 369 (100%)

3) Synthesis of 2β-(5-Hydroxypentyl)-1α,3β,25-tris (triethylsilyloxy)cholesta-5,7-diene:

To a solution of 49 mg (0.059 mmol) of the compound obtained in (2) above in 3 ml of THF was added 340 μl (0.340 mmol) of borine (BH$_3$) (1 mol/l in THF) in an argon atmosphere, followed by stirring at room temperature for 24 hours. To the reaction mixture were added successively 0.5 ml of 3M sodium hydroxide and 0.4 ml of hydrogen peroxide, followed by stirring for 30 minutes. The mixture was extracted with ethyl acetate, and the extract was washed with water and dried over magnesium sulfate. The solvent was removed by distillation, and the resultant residue was purified by fractional thin layer chromatography on silica gel using a 1:10 mixture of ethyl acetate and n-hexane to obtain 14 mg (34%) of the title compound as a colorless oily substance.

$^1$H-NMR (CDCl$_3$)δ: 0.52–0.68(21H,m), 0.91–1.00(33H,m), 1.19(6H,s), 3.60–3.69(2H,m), 3.78(1H,brs), 4.14–4.22(1H, m), 5.28–5.34(1H,m), 5.50–5.60(1H,m)

IR (neat, cm$^{-1}$): 3375 (br), 2950, 2870, 1460, 1380, 1080, 1050, 1010, 820, 740, 730

UV λ$_{max}$ (EtOH) nm: 294, 282, 272

4) Synthesis of 2β-(5-Hydroxypentyl)-1α,3β,25-trihydroxycholesta-5,7-diene:

To a solution of 17 mg (0.020 mmol) of the compound obtained in (3) above in 3 ml of THF was added 302 μl (0.302 mmol) of TBAF (1 mol/l in THF), followed by heating under reflux for 24 hours. Water was added to the reaction mixture, and the reaction mixture was extracted with ethyl acetate. The extract was washed with water and dried over magnesium sulfate. The solvent was removed by distillation, and the resultant residue was purified by fractional thin layer chromatography on silica gel using a 5:1 mixture of dichloromethane and ethanol to obtain 6.2 mg (62%) of the title compound as white crystals.

$^1$H-NMR (CDCl$_3$) δ: 0.63(3H,s), 0.96(3H,d,J=6.3 Hz), 1.02 (3H,s), 1.22(6H,s), 3.65(2H,t,J=6.4 Hz), 3.76(1H,brs), 4.17–4.27(1H,m), 5.32–5.40(1H,m), 5.65–5.72(1H,m)

IR (neat, cm$^{-1}$): 3400 (br), 2960, 2900, 1480, 1070

UV λ$_{max}$ (EtOH) nm: 293, 282, 271

MS m/z : 502 (M$^+$), 59 (100%)

5) Synthesis of 2β-(5-Hydroxypentyl)-1α,3β,25-trihydroxy-9,10-secocholesta-5,7,10(19)-triene:

In 200 ml of ethanol was dissolved 6.2 mg (0.012 mmol) of the compound obtained in (4) above, and the solution was irradiated with light using a 400 W high-pressure mercury lamp/Vycor filter for 90 seconds while bubbling argon gas through the solution under ice-cooling. Subsequently, the solution was heated under reflux for 3 hours. The solvent was removed by distillation, and the resultant residue was purified by fractional thin layer chromatography on silica gel using a 10:1 mixture of dichloromethane and ethanol to obtain 1.4 mg (22%) of the title compound as white crystals.

$^1$H-NMR (CDCl$_3$)δ: 0.55(3H,s), 0.94(3H,d,J=5.9 Hz), 1.22 (6H,s), 3.63(2H,t,J=6.4 Hz), 4.00–4.09(1H,m), 4.10–4.18 (1H,m), 5.02(1H,s), 5.37(1H,s), 6.03(1H,d,J=11.6 Hz), 6.35 (1H,d,J=11.6 Hz)

UV λ$_{max}$ (EtOH) nm: 264

UV λ$_{min}$ (EtOH) nm: 228

MS m/z : 502 (M$^+$), 59 (100%)

EXAMPLE 16

Synthesis of 1α,3β-Dihydroxy-2β-(5-hydroxypentyl)-9,10-secocholesta-5,7,10(19)-triene 1) Synthesis of 1α,3β-Dihydroxy-2β-(4-pentenyl)cholesta-5,7-diene:

To a THF (10 ml) solution of 2.23 ml (18.8 mmol) of 5-bromo-1-pentene was added 458 mg (18.8 mmol) of magnesium in an argon atmosphere, followed by stirring at room temperature for 1 hour. A THF (5 ml) solution of 300 mg (0.75 mmol) of 3β,25-dihydroxy-1α,2α-epoxycholesta-5,7-diene was slowly added thereto dropwise, followed by heat-refluxing for 2 hours. The reaction mixture was poured into a saturated aqueous solution of ammonium chloride and extracted with ethyl acetate. The extract was washed with water and dried over magnesium sulfate. The solvent was removed by distillation, and the resultant residue was purified by fractional thin layer chromatography on silica gel using a 1:1 mixture of ethyl acetate and hexane to obtain 148 mg (43%) of the title compound as a colorless oily substance.

$^1$H-NMR (CDCl$_3$)δ: 0.62(3H,s), 0.87(6H,d,J=6.6 Hz), 0.94 (3H,d,J=6.3 Hz), 1.00(3H,s), 3.77(1H,brs), 4.07–4.21(1H, m), 4.85–5.01(2H,m), 5.30–5.40(1H,m), 5.60–5.69(1H,m), 5.70–5.95(1H,m)

IR (neat, cm$^{-1}$): 3470 (br), 2970, 2880, 1470, 1070, 920, 770

UV λ$_{max}$ (EtOH) nm: 292, 282, 271

MS m/z : 468 (M$^+$), 55 (100%)

2) Synthesis of 1α,3β-Bis(triethylsilyloxy)-2β-(4-pentenyl) cholesta-5,7-diene:

To a solution of 148 mg (0.323 mmol) of the compound obtained in (1) above and 2.33 g (32.3 mmol) of imidazole in 5 ml of DMI was added dropwise 542 ml (3.23 mmol) of TESCl in an argon atmosphere, and the mixture was stirred at room temperature for 48 hours. The reaction mixture was poured into a saturated aqueous solution of sodium chloride and extracted with n-hexane and ethyl acetate. The extract was washed with water and dried over magnesium sulfate. The solvent was removed by distillation, and the resultant residue was purified by fractional thin layer chromatography on silica gel using a 10:1 mixture of n-hexane and ethyl acetate to obtain 143 mg (59%) of the title compound as a colorless oily substance.

$^1$H-NMR (CDCl$_3$)δ: 0.50–0.70(15H,m), 0.88–1.00(30H,m), 3.76(1H,brs), 4.10–4.22(1H,m), 4.90–5.05(2H,m), 5.25–5.35(1H,m), 5.55–5.60(1H,m), 5.70–5.90(1H,m)

IR (neat, cm$^{-1}$): 2940, 2900, 2860, 1450, 1370, 1230, 1080, 1000, 820, 740

UV $\lambda_{max}$ (EtOH) nm: 294, 282, 272

MS m/z : 696 (M$^+$), 442 (100%)

3) Synthesis of 1α,3β-Bis(triethylsilyloxy)2β-(5-hydroxypentyl)cholesta-5,7-diene:

To a solution of 74 mg (0.107 mmol) of the compound obtained in (2) above in 2 ml of THF was added 42.8 ml (0.340 mmol) of borine (BH$_3$) (1 mol/l in THF) in an argon atmosphere, followed by stirring at room temperature for 14 hours. Further, 85.6 ml of borine (1 mol/l in THF) was added thereto, followed by stirring at room temperature for 2 hours. Furthermore, 85.6 ml of borine (1 mol/l in THF) was added thereto, followed by stirring at room temperature for 2 hours. To the reaction mixture were added successively 0.43 ml of 3M sodium hydroxide and 0.36 ml of 30% hydrogen peroxide, followed by stirring at room temperature for 1.5 hours. The mixture was extracted with ethyl acetate, and the extract was washed with water and dried over magnesium sulfate. The solvent was removed by distillation, and the resultant residue was purified by fractional thin layer chromatography on silica gel using a 1:10 mixture of ethanol and dichloromethane to obtain 37 mg (49%) of the title compound as a colorless oily substance.

$^1$H-NMR (CDCl$_3$)δ: 0.54–0.67(15H,m), 0.85–1.02(30H,m), 3.65(2H,t,J=6.4 Hz), 3.75(1H,brs), 4.14–4.22(1H,m), 5.28–5.33(1H,m), 5.55–5.60(1H,m)

IR (neat, cm$^{-1}$): 3350 (br), 2950, 2870, 1460, 1370, 1080, 1050, 1010, 820, 740

UV $\lambda_{max}$ (EtOH) nm: 294, 282, 271

4) Synthesis of 1α,3β-Dihydroxy-2β-(5-hydroxypentyl)cholesta-5,7-diene:

To a solution of 37 mg (0.052 mmol) of the compound obtained in (3) above in 3 ml of THF was added 520 ml (0.520 mmol) of TBAF (1 mol/l in THF) in an argon atmosphere, followed by stirring at room temperature for 48 hours. Water was added to the reaction mixture, and the reaction mixture was extracted with ethyl acetate. The extract was washed with water and dried over magnesium sulfate. The solvent was removed by distillation, and the resultant residue was purified by fractional thin layer chromatography on silica gel using a 10:1 mixture of dichloromethane and ethanol to obtain 19.4 mg (77%) of the title compound as white crystals.

$^1$H-NMR (CDCl$_3$)δ: 0.63(3H,s), 0.87(6H,d,J=6.6 Hz), 0.95 (3H,d,J=6.6 Hz), 1.00(3H,s), 3.59(2H,t,J=6.4 Hz), 3.74(1H, brs), 4.10–4.19(1H,m), 5.33–5.40(1H,m), 5.60–5.65(1H,m)

IR (neat, cm$^{-1}$): 3400 (br), 2960, 2890, 1480, 1390, 1070, 840

UV $\lambda_{max}$ (EtOH) nm: 293, 282, 273

MS m/z : 486 (M$^+$), 55 (100%)

5) Synthesis of 1α,3β-Dihydroxy-2β-(5-hydroxypentyl)-9,10-secocholesta-5,7,10(19)-triene:

In 200 ml of ethanol was dissolved 19.4 mg (0.040 mmol) of the compound obtained in (4) above, and the solution was irradiated with light using a 400 W high-pressure mercury lamp/Vycor filter for 140 seconds while bubbling argon gas through the solution under ice-cooling. Subsequently, the solution was heated under reflux in an argon atmosphere for 3 hours. The solvent was removed by distillation, and the resultant residue was purified by fractional thin layer chromatography on silica gel using a 10:1 mixture of dichloromethane and ethanol to obtain 4.86 mg (22%) of the title compound as white crystals.

$^1$H-NMR (CDCl$_3$)δ: 0.55(3H,s), 0.86(6H,d,J=6.6 Hz), 0.92 (3H,d,J=5.9 Hz), 3.65(2H,t,J=6.4 Hz), 4.00–4.09(1H,m), 4.15(1H,brs), 5.02(1H,s), 5.37(1H,s), 6.03(1H,d,J=11.0 Hz), 6.34(1H,d,J=11.0 Hz)

IR (neat, cm$^{-1}$): 3340 (br), 2950, 2870, 1470, 1380, 1070, 910, 760

UV $\lambda_{max}$ (EtOH) nm: 263

UV $\lambda_{min}$ (EtOH) nm: 228

MS m/z : 486 (M$^+$), 55 (100%)

TEST EXAMPLE 1

Inhibition on Bone Density Reduction in OVX Rat

An SD strain 8-month-old male rat available from Nippon Charles River Co., underwent ovariectomy (OVX) under ether anesthesia. From 2 weeks after the operation, when the wound almost healed up, the compound of Example 2 was orally administered to the OVX rat at a dose of 0.1 pg/kg twice a week for 3 months. The compound was dissolved in edible oil available from The Nisshin Oil Mills, Ltd. (O.D.O.) before use. In addition, a non-treated group which underwent no OVX and received O.D.O. and an OVX group which underwent OVX and received only O.D.O. were prepared.

The bone density of each rat was measured as follows every month from the start of the administration. The rat under anesthesia with Phenobarbital was fixed on its back, and the mean bone density in the 2nd to 5th lumber vertebrae was obtained by measurement with a double X-ray bone salt measuring apparatus DCS-600, manufactured by Aloka Co., Ltd.

The changes of bone density with time in the test group, non-treated group and OVX group are shown in FIG. 1.

TEST EXAMPLE 2

Bone Formation Activity and Serum Ca Elevating Effect in Osteoporosis Model Rat

Figure 2:
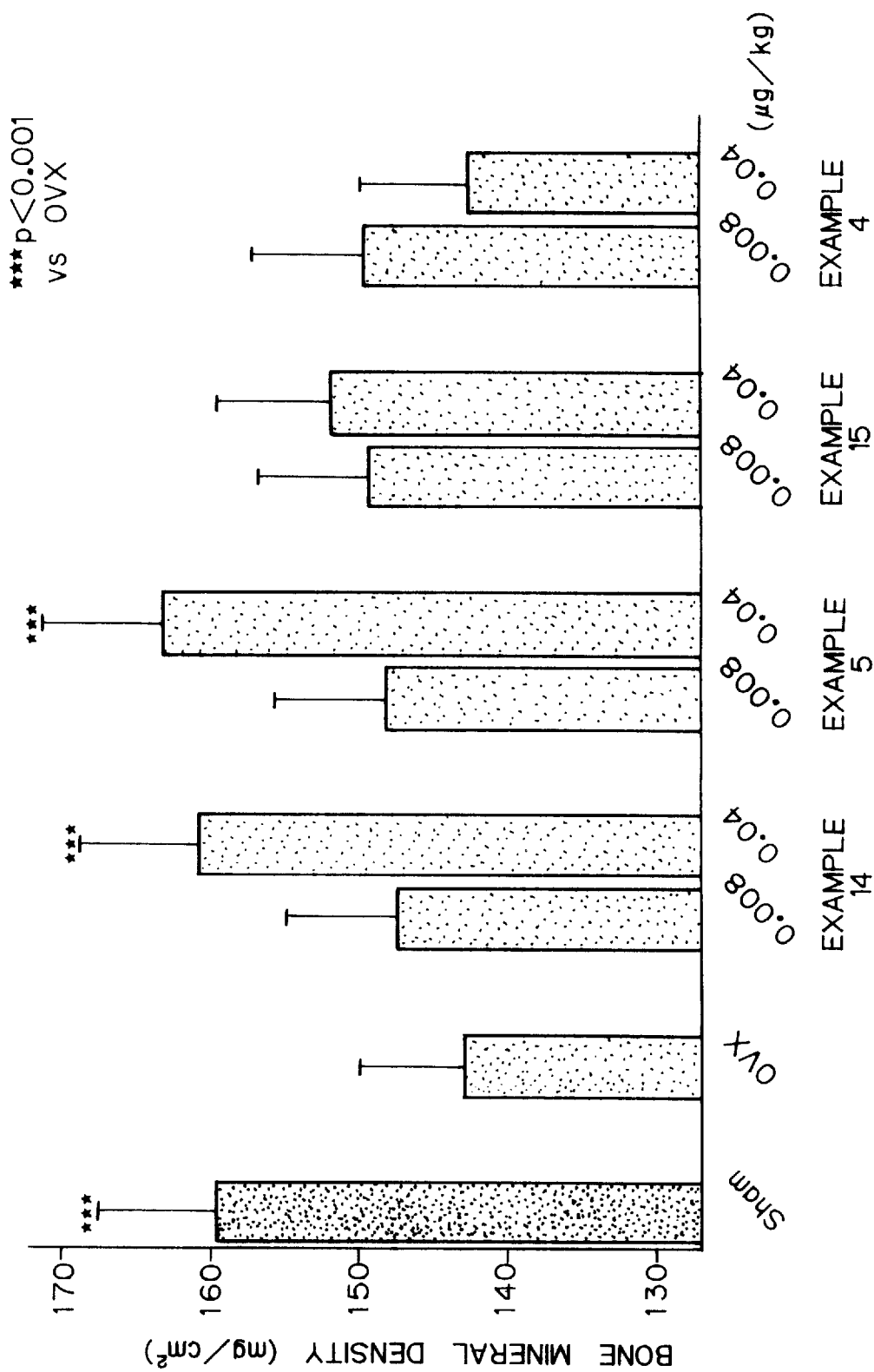
FIG. 2 is a graph showing bone formation activity of the drugs of Examples 4, 5, 14 and 15 in osteoporosis model rats.
Figure 3:
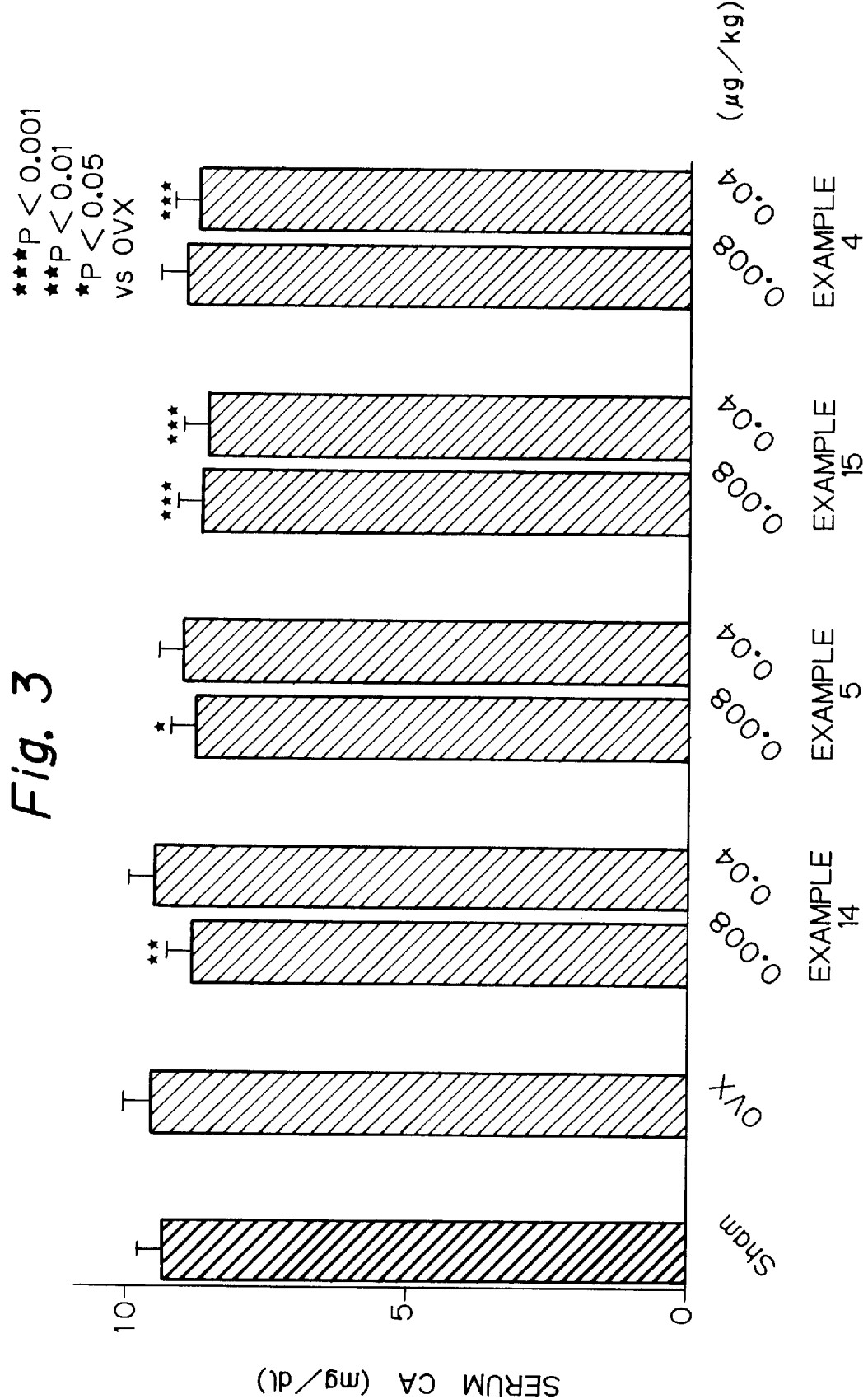
FIG. 3 is a graph showing the influences of the drugs of Examples 4, 5, 14 and 15 on the blood calcium level in osteoporosis model rats.

The bone formation activity of the compounds of Examples 4, 5, 14, and 15 in osteoporosis model rats was determined as follows. A Wistar-Imamichi strain 8-week-old rat underwent OVX or a sham operation. After 2 weeks for postoperative healing, each test compound was orally administered at a dose of 0.008 or 0.04 pg/kg 5 times a week for 6 weeks. During the experimentation, the rats were kept with a normal diet containing 1.2% Ca. After completion of the administration, the bone density in lumber vertebrae was measured in the same manner as in Test Example 1. At the same time, the calcium level in the serum was measured. The results obtained are shown in FIGS. 2 and 3, respectively.

TEST EXAMPLE 3

Bone Formation Activity in Osteoporosis Model Rat

Figure 4:
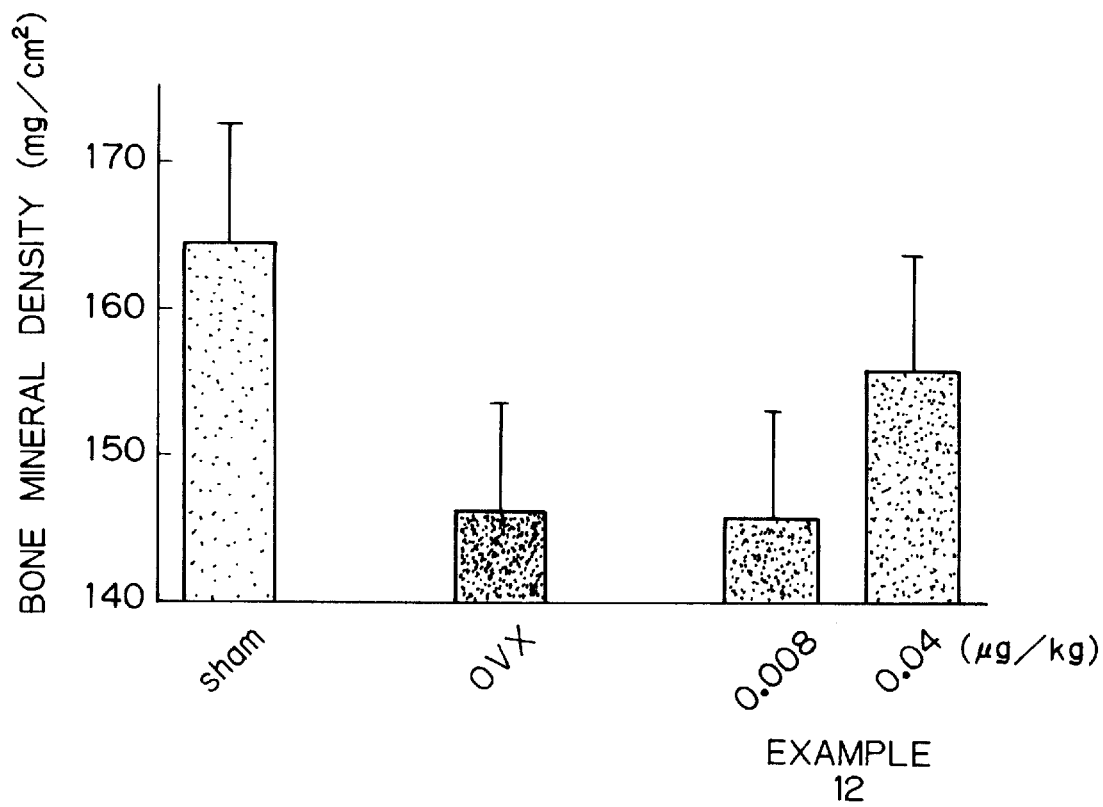
FIG. 4 is a graph showing bone formation activity of the drug of Example 12 in osteoporosis model rats.

The bone formation activity of the compound of Example 12 in osteoporosis model rats was determined as follows. A Wistar-Imamichi strain 8-week-old rat underwent OVX or a sham operation. After 2 weeks for postoperative healing, the test compound was orally administered at a dose of 0.008 or 0.04 pg/kg 5 times a week for 6 weeks. During the experimentation, the rats were kept with a normal diet containing 1.2% Ca. After completion of the administration, the bone density in lumber vertebrae was measured in the same manner as in Test Example 1. The result obtained is shown in FIG. 4.

While the invention has been described in detail and with reference to specific examples thereof, it will be apparent to one skilled in the art that various changes and modifications can be made therein without departing from the spirit and scope thereof.

What is claimed is:

1. A compound represented by formula (I):

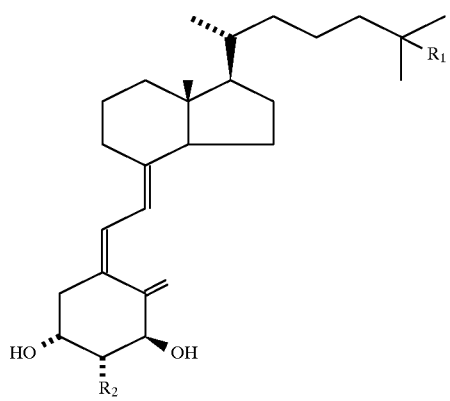

wherein $R_1$ represents a hydrogen atom or a hydroxyl group; and $R_2$ represents a straight-chain or branched $C_1$–$C_7$ alkyl, $C_2$–$C_7$ alkenyl or $C_2$–$C_7$ alkynyl group, which is substituted with a hydroxyl group, a halogen atom, a cyano group, a lower alkoxy group, an amino group or an acylamino group.

2. The compound of claim 1 which is 2β-(4-hydroxybutyl)-1α,3-dihydroxy-9,10-secocholesta-5,7,10(19)-triene.

3. The compound of claim 1 which is 1α,3β-dihydroxy-2β-(6-hydroxyhexyl)-9,10-secocholesta-5,7,10(19)-triene.

4. The compound of claim 1 which is 2β-(6-hydroxyhexyl)-1α,3β,25-trihydroxy-9,10-secocholesta-5,7,10(19)-triene.

5. The compound of claim 1 which is 2β-(4-hydroxybutyl-1α,3β,25-trihydroxy-9,10-secocholesta-5,7,10(19)-triene.

6. The compound of claim 1 which is 2β-(3-hydroxypropyl)-1α,3β,25-trihydroxy-9,10-secocholesta-5,7,10(19)-triene.

7. The compound of claim 1 which is 2β-(5-hydroxypentyl)-1α,3β,25-trihydroxy-9,10-secocholesta-5,7,10(19)-triene.

8. The compound of claim 1 which is 1α,3β-dihydroxy-2β-(5-hydroxypentyl)-9,10-secocholesta-5,7,10(19)-triene.

9. Pharmaceutical composition comprising a pharmacologically effective amount of a compound represented by formula (I):

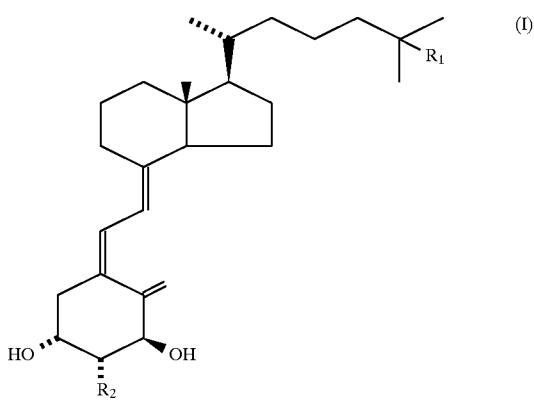

wherein $R_1$ represents a hydrogen atom or a hydroxyl group; and $R_2$ represents a straight-chain or branched $C_1$–$C_7$ alkyl, $C_2$–$C_7$ alkenyl or $C_2$–$C_7$ alkynyl group, which is substituted with a hydroxyl group, a halogen atom, a cyano group, a lower alkoxy group, an amino group or an acylamino group, and a pharmaceutically acceptable carrier.

10. A pharmaceutical composition according to claim 9 wherein said pharmaceutically acceptable carrier comprises an edible oil.

11. A pharmaceutical composition according to claim 9 wherein said compound is 2β-(5-hydroxypentyl)-1α,3β,25-trihydroxy-9,10-secocholestra-5,7,10(19)-triene and said pharmaceutically acceptable carrier comprises an edible food product.

12. A method for treating osteoporosis comprising administering to a patient in need thereof an effective amount of a compound according to claim 1.

13. A method for treating osteoporosis comprising administering to a patient in need thereof an effective amount of a composition according to claim 9.

* * * * *